United States Patent [19]

Gästrin

[11] Patent Number: 4,641,336
[45] Date of Patent: Feb. 3, 1987

[54] FILTER ARRANGEMENT FOR SOFT TISSUE

[75] Inventor: Jan Gästrin, Espoo, Finland

[73] Assignee: Instrumentarium Corp., Finland

[21] Appl. No.: 568,887

[22] Filed: Jan. 6, 1984

[30] Foreign Application Priority Data

Jan. 7, 1983 [FI] Finland .................................. 830043

[51] Int. Cl.$^4$ .............................................. G21K 3/00
[52] U.S. Cl. ...................................... 378/156; 378/159
[58] Field of Search .................................. 378/156–159, 378/5, 49, 150, 151, 152, 156, 157, 158, 159.5; 350/305.1

[56] References Cited

U.S. PATENT DOCUMENTS

| 3,755,672 | 8/1973 | Edholm et al. | 378/158 |
| 4,181,858 | 1/1980 | Moore | 378/159 |
| 4,347,440 | 8/1982 | Haas | 378/156 |

FOREIGN PATENT DOCUMENTS

| 1145277 | 5/1963 | Fed. Rep. of Germany | 378/157 |
| 3035435 | 4/1981 | Fed. Rep. of Germany | 378/38 |
| 3011912 | 10/1981 | Fed. Rep. of Germany | 378/158 |

OTHER PUBLICATIONS

"Deutsche Stomatologie", vol. 9, 1969.

Primary Examiner—Craig E. Church
Assistant Examiner—Charles Wieland
Attorney, Agent, or Firm—Andrus, Sceales, Starke & Sawall

[57] ABSTRACT

The invention relates to a soft tissue filter arrangement in X-ray imaging of a patient's skull by means of a chefalostat, wherein a patient (P) is by means of ear plugs (5) or the like supports preferably fixed relative to imaging coordinates as well as by means of a nasion and/or forehead support (6) set in a determined position and location between an X-ray source (1) and a film (4) or the like imaging medium and wherein the X-ray source is provided with diaphragm (2) for directing X-rays to the patient and restricting them to a proper sized beam (3) for imaging. The arrangement comprises preferably V-shaped filter means (7) whose position relative to the soft tissues of a patient's face in a cross-sectional plane perpendicular to the X-ray beam is adapted to be set on the basis of a distance (D) between said ear plugs (5) or the like supports and said nasion and/or forehead support (6) or on the basis of a patient's skull dimension correlating sufficiently well therewith. The nasion and/or forehead support (6) can be preferably provided with control elements and a scale by means of which the control elements (8) of said filter means (7) can be adapted to be controlled for producing an image having optimum patientwise exposure.

7 Claims, 2 Drawing Figures

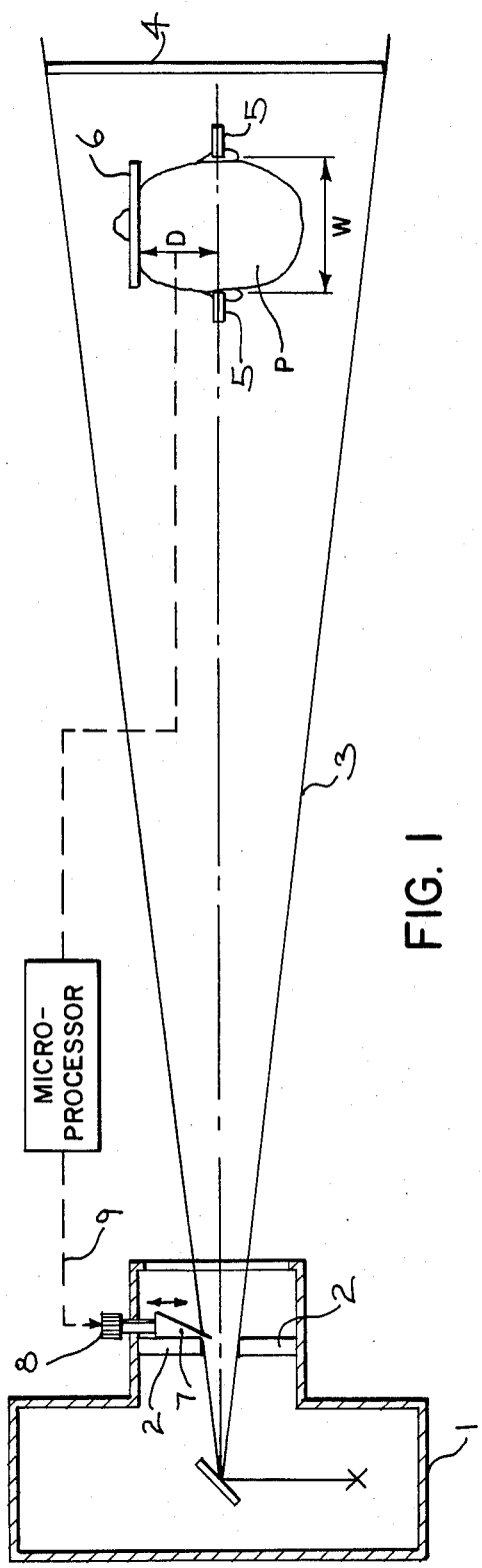
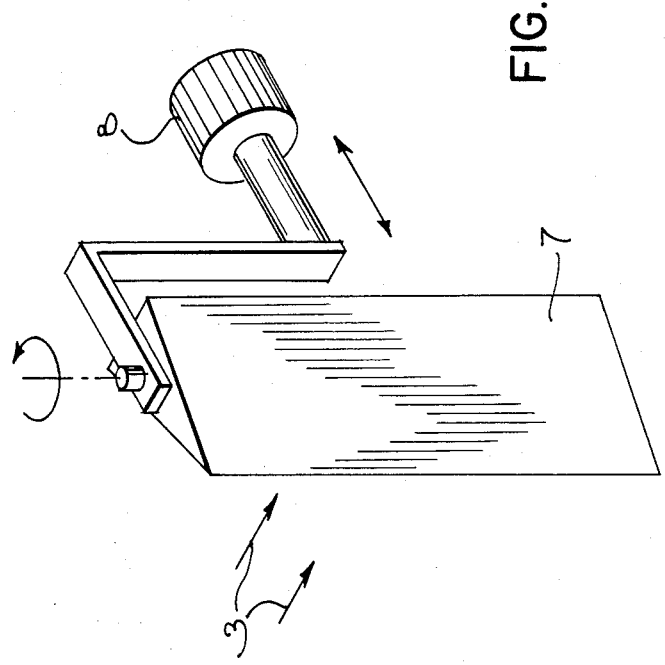
FIG. 1
FIG. 2

FILTER ARRANGEMENT FOR SOFT TISSUE

The present invention relates to a soft tissue filter arrangement.

BACKGROUND OF THE INVENTION

In cephalometry, the skull of a patient is X-rayed on a film from the side. Visible in a conventional X-ray image is then primarily the bone structure of a skull. It is often desirable, however, that the soft facial tissues of a patient would also be visible to a certain degree in a patient's skull. For this purpose, it is known in the art to adapt between the patient's skull and the film a V-shaped X-ray absorbing filter which prevents the X-radiation, which is penetrated through soft tissues and is in abundance with respect to the bony parts of a skull, from exposing the film too much on these areas as otherwise said soft tissues are not at all visible on the film. Since the shape and size of the patient's skulls differ considerably from each other, the position of said filter must be set patientwise in order to obtain each time an image exposed as properly as possible also for soft tissues. In practice, the positioning and setting of a filter is done by the operator according to his own judgement with the consequence that up to ⅔ of the images may be failures because of wrong filter position, in which case a patient may have to be re-exposed to X-radiation.

SUMMARY OF THE PRESENT INVENTION

An object of the invention is to eliminate the prior art deficiencies by providing a novel soft tissue filter arrangement whereby the setting of a soft tissue filter can be effected in a simple and reliable manner, so that proper exposure of the images can be ensured in most cases. Another object of the invention is to reduce an X-radiation dose received by a patient. According to the invention, the position of soft tissue filter means is determined on the basis of the accurate distance between earplugs or the like supports and a nasion and/or forehead support or measuring means used for setting up a patient. If the imaging coordinates are set on the basis of the patient's ear cavity, the consideration and utilization of the variation of said distance for the patientwise positioning of filter means improves substantially the possibilities of exposing soft tissues patientwise correctly. In most cases, re-imagings can be avoided this way. Furthermore, the X-radiation dose received by the patient can be reduced by positioning said filter means between a source of X-rays and a patient and by supporting said means e.g. on shutter means or on the body of an X-ray tube itself.

BRIEF DESCRIPTION OF THE DRAWING

The invention will now be described in more detail with reference made to the accompanying drawing in which FIG. 1 is a top view of a filter arrangement of the invention; and FIG. 2 is a partial perspective view of a modification thereof.

DETAILED DESCRIPTION OF THE INVENTION

In the drawing, reference numeral 1 designates an X-ray tube which generates X-radiation that is directed to a patient P and restricted to a suitable beam of rays 3 for imaging by diaphragm 2. The radiation penetrated through the patient is recorded on a film 4. X-ray tube 1 and the support of film 4 are preferably fixed together for providing fixed imaging coordinates (not shown in figure). The patient is positioned on the imaging coordinates by means of ear plugs 5 or the like supports. This is to ensure that a given part of each patient, e.g. the ear cavity, will be imaged on the same spot in a film square. The device also comprises an adjustable nasion and/or forehead support 6 whose distance from ear plugs is indicated with D. Thus, this distance is a patientwise measure the same way as the mutual distance between ear plugs, i.e. the width dimension W of a patient's skull. According to the invention, dimension D is utilized for the adjustment of soft tissue filter means 7. This dependence and adjustment is designated by a control signal 9. The adjustment can be effected manually by a control knob 8 which is preferably fitted with a proper control scale. Also for distance D, the apparatus is provided with a numerical control scale according to which said control knob scale is preferably precalibrated for facilitating the adjustment. The control scale of distance D and setting mechanisms of support or measuring means 6 as well as setting mechanisms of supports 5 are not illustrated in detail in the figure, as they represent conventional technology and are generally available in cephalostats. In practice, ear plugs 5 are in the cross-sectional plane perpendicular to X-rays bound to the imaging coordinates, whereby the patientwise variation of dimension D is effected by adjusting support or measuring means 6.

Instead of the above-described manual control, the adjustment of filter means 7 can be preferably automated in a manner that the control elements of filter means 7 are directly controlled to effect necessary resetting actions on the basis of the dimensional data obtained of the patientwise positioning e.g. by means of sensor elements. When effected by means of modern microprocessor technology, the question is merely about a simple programming procedure.

Since it is also rather simple to find out dimension W or the width of a patient's skull from cephalostats by means of ear supports 5, said dimension generally correlating rather well with dimension D, said control of filter means may be effected also on the basis of dimension W, if so desired. Also, supporting of filter means 7 can of course be effected in a manner different from the figure. The essential point is to effect the positional control of filter means in a controllable manner with respect to imaging coordinates.

In addition to the position of a soft tissue filter, it may become necessary to adjust the slope or V-shape of a filter, which depends on the width of a patient's skull. The slope control can be effected e.g. by adapting the filter means to be rotatable around an axis substantially perpendicular to X-rays and to the direction in which the position of filter means is displaced. See FIG. 2.

The invention is not limited to the above-described embodiment but a plurality of modifications thereof are conceivable within the scope of the annexed claims.

I claim:

1. A soft tissue filter arrangement for providing proper soft tissue exposure in combination with a cephalographic apparatus that images a patient's skull in a sagittal plane, said cephalographic apparatus having a source projecting an X-ray beam along a line of projection extending from the source to an imaging medium, said apparatus having a pair of spaced positioning means disposed between the X-ray beam source and the imaging medium, said pair of positioning means defining a line extending intermediate them that is perpendicular to the imaging medium, said positioning means being engagable with the sides of the patient's head for positioning the skull of the patient with the sagittal plane parallel to the imaging means, said soft tissue filter arrangement comprising:
  measuring means located opposite the positioning means and spaced therefrom in a direction normal to the intermediate line, said measuring means being movable toward and away from the positioning means in the direction normal to the intermediate line for application to one of the forehead or nasion of the patient, said measuring means providing an indication of the dimension between said measuring means when applied to the forehead or nasion and the intermediate line of the positioning means, said dimension being measured in a direction parallel the patient's sagittal plane; and
  a generally V-shaped X-ray filter means of fixed shape, said filter means being located to one side of said measuring means and the positioning means with respect to the X-ray beam line of projection, said filter means being adjustably insertable in the X-ray beam normal to the line of projection in accordance with the indication obtained from said measuring means for being positioned relative to the soft tissue of the patient.

2. A soft tissue filter arrangement as set forth in claim 1 wherein said measuring means is provided with a scale for determination of a numerical indication representing the dimension for adjustably positioning said filter means.

3. A soft tissue filter arrangement as set forth in claim 1 wherein said filter means is provided with a scale corresponding to that of said measuring means for adjustably positioning said filter means.

4. A soft tissue arrangement as set forth in claim 1 wherein said positioning means engages the ears of the patient and wherein said measuring means determines the distance between the forehead or nasion and a frontal plane extending through the ears of the patient and provides and indication thereof.

5. A soft tissue filter arrangement as set forth in claim 1 wherein said filter means is operated by a control means responsive to a control signal derived from the dimension determined by the application of the measuring means to the patient.

6. A soft tissue filter arrangement as set forth in claim 1 wherein the cephalographic apparatus includes a diaphragm means for controlling the size of the projected X-ray beam and wherein said filter means is mounted on said diaphragm means.

7. A soft tissue filter arrangement as set forth in claim 1 wherein said filter means is rotatable about an axis substantially perpendicular to the line of projection of the beam of X-rays.

* * * * *